US012778523B2

(12) United States Patent
Li et al.

(10) Patent No.: US 12,778,523 B2

(45) Date of Patent: Nov. 3, 2026

(54) METHODS AND SYSTEMS FOR IMAGE PROCESSING

(71) Applicant: UNITED IMAGING HEALTHCARE NORTH AMERICA, INC., Houston, TX (US)

(72) Inventors: Tiantian Li, Houston, TX (US); Hongdi Li, Houston, TX (US)

(73) Assignee: UNITED IMAGING HEALTHCARE NORTH AMERICA, INC., Houston, TX (US)

( * ) Notice: Subject to any disclaimer, the term of this patent is extended or adjusted under 35 U.S.C. 154(b) by 140 days.

(21) Appl. No.: 18/603,236

(22) Filed: Mar. 13, 2024

(65) Prior Publication Data

US 2025/0288263 A1 Sep. 18, 2025

(51) Int. Cl.

| | |
|---|---|
| ***A61B 6/03*** | (2006.01) |
| ***G06T 7/10*** | (2017.01) |
| ***G06T 7/20*** | (2017.01) |

(52) U.S. Cl.

CPC ................ *A61B 6/037* (2013.01); *G06T 7/10* (2017.01); *G06T 7/20* (2013.01)

(58) Field of Classification Search

None

See application file for complete search history.

(56) References Cited

U.S. PATENT DOCUMENTS

| | | | | |
|---|---|---|---|---|
| 2005/0226527 | A1* | 10/2005 | Weese | G06T 7/20 382/275 |
| 2011/0288407 | A1 | 11/2011 | Brinks et al. | |
| 2014/0217294 | A1 | 8/2014 | Rothfuss et al. | |
| 2018/0116621 | A1 | 5/2018 | Berker et al. | |
| 2023/0003909 | A1 | 1/2023 | Hamill | |

FOREIGN PATENT DOCUMENTS

| | | | |
|---|---|---|---|
| CN | 103220978 | A | 7/2013 |
| CN | 102449504 | B | 2/2015 |
| CN | 113712584 | A | 11/2021 |
| CN | 115018946 | A | 9/2022 |
| WO | 2022007353 | A1 | 1/2022 |

* cited by examiner

*Primary Examiner* — Edwin C Gunberg

(74) *Attorney, Agent, or Firm* — METIS IP LLC

(57) ABSTRACT

Systems and methods for image processing are provided. The methods may include obtaining first positron emission tomography (PET) data and second PET data of a subject. The methods may include determining, based on the first PET data, first reference data relating to first target events occurred in the first PET scan. The first target events at least include first backscatter events. The methods may include determining, based on the second PET data, second reference data relating to second target events occurred in the second PET scan. The second target events at least include second backscatter events. The methods may further include determining a motion vector field based on the first reference data and the second reference data.

20 Claims, 9 Drawing Sheets

METHODS AND SYSTEMS FOR IMAGE PROCESSING

TECHNICAL FIELD

The present disclosure relates to the field of medical imaging, in particular to, methods and systems for positron emission tomography (PET) image processing.

BACKGROUND

PET has been widely used in clinical diagnosis and/or treatment. Before a PET scan, a radioactive tracer may be injected into a subject. A positron generated by the decay of the radioactive tracer may travel within the subject and interact with an electron in the subject. The positron and the electron may annihilate, thus producing a pair of gamma photons with opposite propagation directions. A detector of a PET scanner may detect the pair of gamma photons. The position of the annihilation may be estimated based on a detection time difference of the pair of gamma photons, and a distribution map (i.e., a PET image) of the radioactive tracer in the subject may be reconstructed based on the estimated position. It is desirable to provide methods and systems for PET image processing to improve the quality of the PET image.

SUMMARY

An aspect of the present disclosure relates to a method for image processing. The method may be implemented on a computing device including at least one processor and at least one storage device. The method may include obtaining first positron emission tomography (PET) data and second PET data of a subject. The method may include determining, based on the first PET data, first reference data relating to first target events occurred in the first PET scan. The first target events at least include first backscatter events. The method may include determining, based on the second PET data, second reference data relating to second target events occurred in the second PET scan. The second target events at least include second backscatter events. The method may further include determining a motion vector field based on the first reference data and the second reference data.

In some embodiments, the first target events further include first background events, the second target events further include second background events, the first background events and the second background events are caused by radioactive decay of a crystal material.

In some embodiments, the first reference data and the second reference data are determined by determining coincident windows, the coincident windows including a first energy window, a second energy window, and a time window; determining, based on the first PET data and the coincident windows, the first reference data relating to the first target events occurred in the first PET scan; and determining, based on the second PET data and the coincident windows, the second reference data relating to the second target events occurred in the second PET scan.

In some embodiments, the determining a motion vector field based on the first reference data and the second reference data includes generating a first attenuation image of the subject based on the first reference data; generating a second attenuation image of the subject based on the second reference data; and determining the motion vector field based on the first attenuation image and the second attenuation image of the subject.

In some embodiments, the generating a first attenuation image of the subject based on the first reference data includes one or more iterations. Each of the iterations comprises determining an initial attenuation image and an initial PET image of the iteration; determining third reference data relating to third target events occurred in a blank scan without the subject based on the initial attenuation image and the initial PET image; generating an updated attenuation image by updating the initial attenuation image based on the third reference data and the first reference data; generating an updated PET image by updating the initial PET image based on the updated attenuation image and the first PET data; and determining the first attenuation image of the subject based on the updated PET image.

In some embodiments, the third target events include third backscatter events and third background events. The determining third reference data includes determining the third reference data relating to the third backscatter events based on the initial attenuation image and the initial PET image; obtaining blank scan data collected by performing the blank scan; and determining the third reference data relating to the third background events based on the blank scan data.

In some embodiments, each iteration further comprises determining fourth reference data relating to scatter events in the first target events and fifth reference data relating to random events in the first target events. The updated attenuation image is determined further based on the fourth reference data and the fifth reference data.

In some embodiments, the method may further include obtaining an anatomical image; generating a corrected anatomical image matching a PET image corresponding to the second PET data by processing the anatomical image based on the motion vector field; and generating an attenuation corrected PET image based on the PET image and the corrected anatomical image.

In some embodiments, the anatomical image includes a computed tomography (CT) image or a magnetic resonance (MR) image.

In some embodiments, the first PET data is collected by a first PET scan performed on the subject at a first time, and the second PET data is collected by a second PET scan performed on the subject at a second time In some embodiments, the anatomical image is collected by an anatomical scan performed on the subject at the first time.

In some embodiments, the anatomical image is collected by an anatomical scan performed on the subject at any time other than the first time and the second time.

In some embodiments, the second time is before or after the first time, and the second PET scan is performed before or after the first PET scan.

In some embodiments, the method may further include obtaining an anatomical image; generating a corrected anatomical image matching a PET image corresponding to the second PET data by processing the anatomical image based on the motion vector field; and performing at least one of image segmentation or treatment plan planning based on at least the corrected anatomical image.

A further aspect of the present disclosure relates to a system. The system may include at least one storage device including a set of instructions and at least one processor in communication with the at least one storage device. When executing the set of instructions, the at least one processor may be directed to cause the system to implement operations. The operations may include obtaining first positron emission tomography (PET) data and second PET data of a subject. The operations may include determining, based on the first PET data, first reference data relating to first target events occurred in the first PET scan. The first target events at least include first backscatter events. The operations may include determining, based on the second PET data, second reference data relating to second target events occurred in the second PET scan. The second target events at least include second backscatter events. The operations may further include determining a motion vector field based on the first reference data and the second reference data.

A still further aspect of the present disclosure relates to a non-transitory computer readable medium including executable instructions. When the executable instructions are executed by at least one processor, the executable instructions may direct the at least one processor to perform a method. The method may include obtaining first positron emission tomography (PET) data and second PET data of a subject. The method may include determining, based on the first PET data, first reference data relating to first target events occurred in the first PET scan. The first target events at least include first backscatter events. The method may include determining, based on the second PET data, second reference data relating to second target events occurred in the second PET scan. The second target events at least include second backscatter events. The method may further include determining a motion vector field based on the first reference data and the second reference data.

Additional features may be set forth in part in the description which follows, and in part may become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
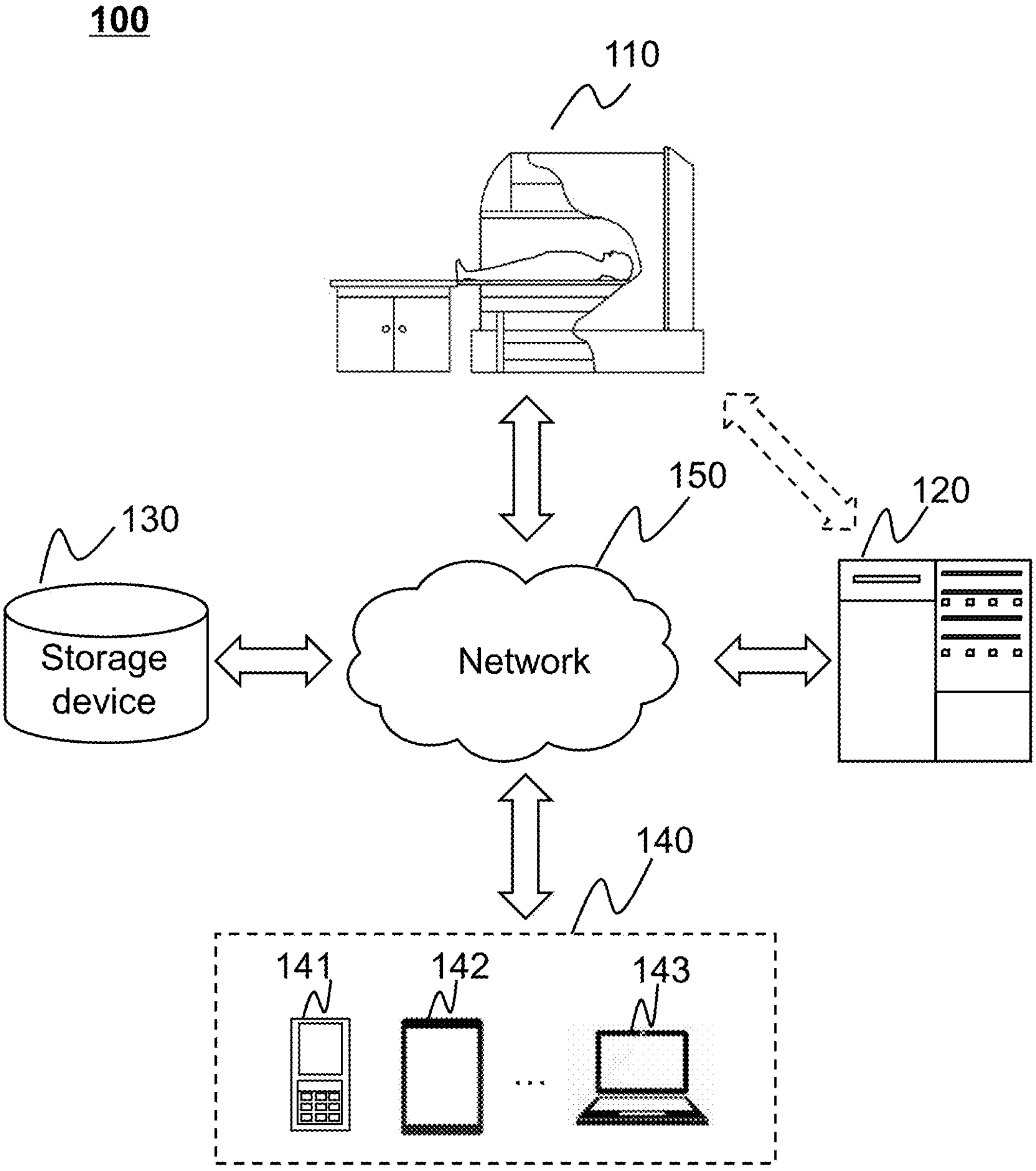
FIG. 1 is a schematic diagram illustrating an exemplary image processing system according to some embodiments of the present disclosure.

In the following detailed description, numerous specific details may be set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments may be readily apparent to those skilled in the art, and the general principles defined herein may be applied to other embodiments and applications without departing from the spirit and scope of the present disclosure. Thus, the present disclosure may be not limited to the embodiments shown, but to be accorded the widest scope consistent with the claims.

The terminology used herein may be for the purpose of describing particular example embodiments only and may be not intended to be limiting. As used herein, the singular forms "a," "an," and "the" may be intended to include the plural forms as well, unless the context clearly indicates otherwise. It may be understood that the terms "system," "unit," "module," and/or "block" used herein are one method to distinguish different components, elements, parts, sections, or assemblies of different levels in ascending order. However, the terms may be displaced by another expression if they achieve the same purpose.

The modules (or units, blocks, units) described in the present disclosure may be implemented as software and/or hardware modules and may be stored in any type of non-transitory computer-readable medium or other storage devices. In some embodiments, a software module may be compiled and linked into an executable program. It may be appreciated that software modules may be callable from other modules or from themselves, and/or may be invoked in response to detected events or interrupts. Software modules configured for execution on computing devices may be provided on a computer-readable medium or as a digital download (and can be originally stored in a compressed or installable format that requires installation, decompression, or decryption prior to execution). Such software code may be stored, partially or fully, on a memory device of the executing computing device, for execution by the computing device. Software instructions may be embedded in a firmware, such as an EPROM. It may be further appreciated that hardware modules (e.g., circuits) may be included in connected or coupled logic units, such as gates and flip-flops, and/or may be included in programmable units, such as programmable gate arrays or processors. The modules or computing device functionality described herein may be preferably implemented as hardware modules, but may be software modules as well. In general, the modules described herein refer to logical modules that may be combined with other modules or divided into units despite their physical organization or storage.

Certain terminology has been used to describe embodiments of the present disclosure. For example, the terms "one embodiment," "an embodiment," and/or "some embodiments" may mean that a particular feature, structure, or characteristic described in connection with the embodiment is in at least one embodiment of the present disclosure. Therefore, it is emphasized and should be appreciated that two or more references to "an embodiment" or "one embodiment" or "an alternative embodiment" in various portions of this specification may not necessarily all referring to the same embodiment. Furthermore, the particular features, structures, or characteristics may be combined as suitable in one or more embodiments of the present disclosure.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings may be for the purpose of illustration and description only and may be not intended to limit the scope of the present disclosure.

The flowcharts used in the present disclosure may illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

PET has been widely used in clinical examination and disease diagnosis. Normally, before a PET scan is performed by a PET scanner, a radioactive tracer (also referred to as a radioactive isotope) may be injected into a subject to be scanned. For example, the radioactive tracer may be generated by marking a material necessary for biological life metabolism (e.g., glucose, protein, nucleic acid, fatty acid, etc.) with a short-life radionuclide (e.g., 18F, 11C, etc.). One or more atoms of the radioactive tracer may be chemically incorporated into biologically active molecules in the subject. The active molecules may become concentrated in a tissue of interest within the subject. The radioactive tracer may undergo positron emission decay and emit positrons. A positron may travel a short distance (e.g., about 1 mm) within the tissue of interest, lose kinetic energy, and interact with an electron of the subject. The positron and the electron may annihilate and produce a pair of annihilation photons (e.g., annihilation photons having an energy level of 511 keV). The pair of annihilation photons (or radiation rays) may move in approximately opposite directions, and be detected by a detector of the PET scanner. PET data collected by the detector in the PET scan may be processed to reconstruct a PET image of the subject.

In the process of PET image reconstruction, physical correction, such as an attenuation correction, may need to be performed on the PET data. Typically, PET/computed tomography (CT) imaging technology is used to obtain PET and CT data of a subject simultaneously. The CT data provide tissue density information of the subject, which can be used to determine tissue attenuation coefficients of different portions (e.g., different organs, different tissues) of the subject and attenuation coefficients of the different portions of the subject with respect to 511 Kev photons. The attenuation coefficients are then applied to the PET data to eliminate the attenuation effect of the subject with respect to the 511 Kev photons, thereby achieving the attenuation correction of the PET image. During treatment, multiple PET/CT scans are often required to evaluate the effectiveness of the treatment plan over the whole treatment process. In order to reduce the high radiation dose caused by multiple CT scans, usually only one PET/CT scan is performed at a first time (e.g., during the first treatment session), and PET scans are performed at other second times (e.g., during other treatment sessions). By performing image registration based on CT data and PET data obtained at the first time and PET data obtained at the other second times, CT images corresponding to the second times are generated and used to perform attenuation correction for PET images at the other second times.

However, the accuracy of the image registration is highly dependent on the quality of the PET images acquired at the first time and the second time, so for some PET images acquired with low-doses, the accuracy of the image registration will be significantly reduced. Moreover, the pixel value distribution of a PET image is related to the distribution of the radioactive tracer in the subject. In addition, even if PET data and CT data are collected at in the same PET/CT scan at the first time, there may still be mismatch between the PET data and the CT data due to subject movement and therefore cause image registration failures. Some highly selective and specific radioactive tracers, such as Zirconium-89 used to label monoclonal antibodies, only can be used to target the location of lesions and do not provide anatomical information, resulting in failure of image registration.

The present disclosure provides systems and methods for image processing. The systems may obtain an anatomical image (e.g., a CT image, a magnetic resonance (MR) image), first PET data, and second PET data of a subject. The anatomical image is collected by an anatomical scan performed on the subject at a first time, the first PET data is collected by a first PET scan performed on the subject at the first time, and the second PET data is collected by a second PET scan performed on the subject at a second time after the first time. The systems may determine, based on the first PET data, first reference data relating to first target events occurred in the first PET scan. The first target events at least include first backscatter events and/or first background events. The systems may determine, based on the second PET data, second reference data relating to second target events occurred in the second PET scan. The second target events at least include second backscatter events and/or second background events. The systems may determine a motion vector field based on the first reference data and the second reference data. Further, the systems may generate a corrected anatomical image matching the PET image by warping/processing the anatomical image based on the motion vector field and generating an attenuation corrected PET image based on the PET image and the corrected anatomical image.

In the embodiments of the present disclosure, reference data relating to backscatter events and/or background events are determined and used for determining the motion vector field.

A backscatter event occurs when a first particle and a second particle generated by an annihilation photon (also referred to as an original annihilation photon) are detected by crystal units of a PET scanner within a certain time window. In some occasions, the annihilation photon may collide with and be detected by a crystal unit of the scanner, undergo scattering in the crystal unit of the scanner, and be bounced back from the crystal unit and travel through the subject again; the bounced annihilation photon may be detected by another crystal unit. A backscatter even occurs when the original annihilation photon and the bounced annihilation photon are detected within a certain time window. The data relating to the first backscatter events and the first PET data are collected at the same time, and the data relating to the second backscatter events and the second PET data are collected at the same time, so that there is no risk of image registration failure due to subject movement and high selectivity and specificity of the radioactive tracers. In addition, the backscatter events occur during the PET scan (e.g., the first PET scan, the second PET scan), so that no additional radiation dose is added to the subject.

A background event occurs when a first particle and a second particle generated by the radioactive decay of the crystal material (e.g., Lu-176) are detected by crystal units of a PET scanner within a certain time window. If the radioactive decay of Lu-176 occurs in a crystal unit, the beta electron generated by the radioactive decay may be detected in one crystal unit, and one or more of the gamma photons generated by the radioactive decay may escape from the crystal unit and be detected by other crystal unit(s). If a beta electron and a gamma photon produced by the radioactive decay of Lu-176 are detected by different crystal units within a certain time window, it may be determined that a background event occurs. The background events are independent of the distribution of the radioactive tracers in the subject, so that there is no risk of image registration failure due to subject movement and high selectivity and specificity of the radioactive tracers. The backscatter events and/or the background events are determined based on the PET data (e.g., the first PET data, the second PET data), so that there is no need to add additional acquisition processes and equipment. The background events occur in the LSO and LYSO material of the crystal unit of the scanner, and backscattering events occur in many other crystal materials (e.g., BGO) of the crystal unit of the scanner, so that the image processing methods and systems provided in the present disclosure have a wide range of applications.

FIG. 1 is a schematic diagram illustrating an exemplary image processing system according to some embodiments of the present disclosure. As shown in FIG. 1, the image processing system 100 may include a scanner 110, a processing device 120, a storage device 130, a terminal 140, and a network 150. In some embodiments, the scanner 110, the processing device 120, the storage device 130, and/or the terminal 140 may be connected to and/or communicate with each other via a wireless connection, a wired connection, or a combination thereof.

The scanner 110 may be configured to scan a subject to acquire image data of the subject. In some embodiments, the scanner 110 performs a PET scan on the subject to obtain PET data of the subject. In some embodiments, the scanner 110 performs an anatomical scan (e.g., a CT scan, an MR scan) on the subject to obtain an anatomical image (e.g., a CT image or an MR image) of the subject. In some embodiments, the scanner 110 simultaneously performs the PET scan and the anatomical scan on the subject to obtain the PET data and the anatomical image of the subject. Merely by way of example, the scanner 110 includes a PET-CT scanner, a single-photon emission computed tomography (SPECT)-CT scanner, a PET-MR scanner, a SPECT-MR scanner, or the like. For illustration purposes, the following descriptions are provided with reference to a PET-CT scanner, and this is not intended to be limiting.

In some embodiments, the subject includes a human being (e.g., a patient), an animal, or a specific portion, organ, and/or tissue thereof. Merely by way of example, the target subject includes head, chest, abdomen, heart, liver, upper limbs, lower limbs, or the like, or any combination thereof. In the present disclosure, the term "object" or "subject" are used interchangeably in the present disclosure.

In some embodiments, the processing device 120 is a single server or a server group. The server group may be centralized or distributed. The processing device 120 may process data and/or information obtained from the scanner 110, the storage device 130, and/or the terminal 140. For example, the processing device 120 obtains an anatomical image, first PET data collected by a first PET scan, and second PET data collected by a second PET scan of the subject from the scanner 110. Based on the first PET data, the processing device 120 may determine first reference data relating to first target events occurred in the first PET scan. Based on the second PET data, the processing device 120 may determine second reference data relating to second target events occurred in the second PET scan. Further, the processing device 120 may determine a motion vector field based on the first reference data and the second reference data.

In some embodiments, the processing device 120 may be local or remote from the image processing system 100. In some embodiments, the processing device 120 may be implemented on a cloud platform. In some embodiments, the processing device 120 or a portion of the processing device 120 may be integrated into the scanner 110 and/or the terminal 140. It should be noted that the processing device 120 in the present disclosure may include one or multiple processors. Thus operations and/or method steps that are performed by one processor may also be jointly or separately performed by the multiple processors.

The storage device 130 may store data, instructions, and/or any other information. In some embodiments, the storage device 130 may store data obtained from the scanner 110, the processing device 120, and/or the terminal 140. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or a combination thereof. In some embodiments, the storage device 130 may be implemented on a cloud platform. In some embodiments, the storage device 130 may be part of the scanner 110, or the processing device 120, or the terminal 140.

The terminal 140 may be configured to enable user interactions between a user and the image processing system 100. In some embodiments, the terminal 140 may be connected to and/or communicate with the scanner 110, the processing device 120, and/or the storage device 130. In some embodiments, the terminal 140 may include a mobile device 141, a tablet computer 142, a laptop computer 143, or the like, or a combination thereof. In some embodiments, the terminal 140 may be part of the processing device 120 and/or the scanner 110.

The network 150 may include any suitable network that can facilitate the exchange of information and/or data for the image processing system 100. In some embodiments, one or more components of the image processing system 100 (e.g., the scanner 110, the processing device 120, the storage device 130, the terminal 140, etc.) may communicate information and/or data with one or more other components of the image processing system 100 via the network 150.

It should be noted that the above description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. In some embodiments, the image processing system 100 may include one or more additional components and/or one or more components described above may be omitted. Additionally or alternatively, two or more components of the image processing system 100 may be integrated into a single component. For example, the processing device 120 may be integrated into the scanner 110. As another example, a component of the image processing system 100 may be replaced by another component that can implement the functions of the component. However, those variations and modifications do not depart from the scope of the present disclosure.

Figure 2:
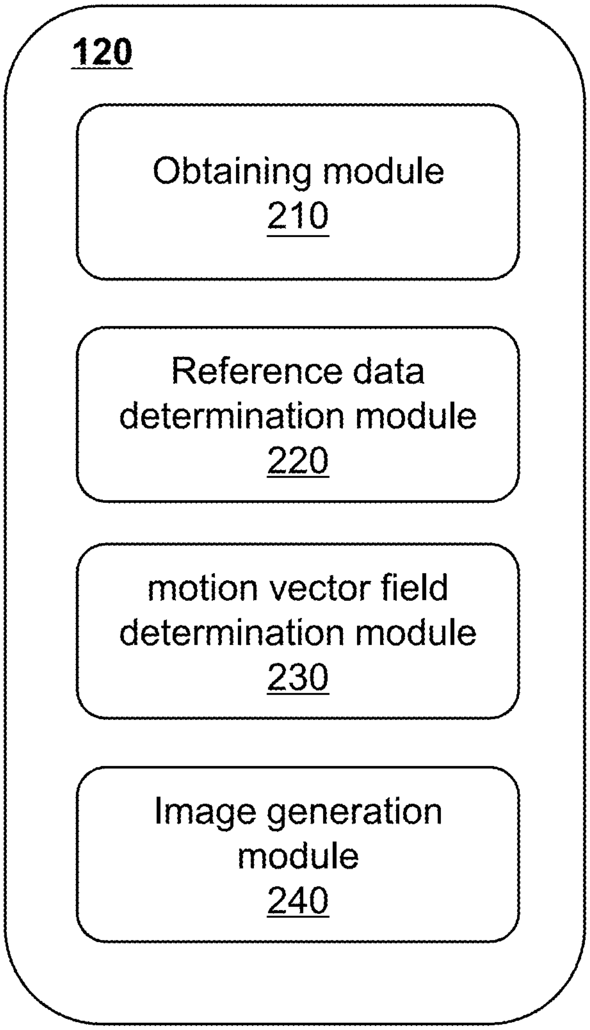
FIG. 2 is a block diagram illustrating an exemplary processing device according to some embodiments of the present disclosure.

FIG. 2 is a block diagram illustrating an exemplary processing device according to some embodiments of the present disclosure. As shown in FIG. 2, the processing device 120 may include an obtaining module 210, a reference data determination module 220, a motion vector field determination module 230, and an image generation module 240.

The obtaining module 210 may be configured to obtain an anatomical image, first PET data, and second PET data of a subject. More descriptions of the obtaining of the anatomical image, the first PET data, and the second PET data may be found elsewhere in the present disclosure (e.g., operation 310 and the descriptions thereof).

The reference data determination module 220 may be configured to determine, based on the first PET data, first reference data relating to first target events occurred in the first PET scan and determine, based on the second PET data, second reference data relating to second target events occurred in the second PET scan. More descriptions of the determination of the first reference data and the second reference data may be found elsewhere in the present disclosure (e.g., operations 320-330 and the descriptions thereof).

The motion vector field determination module 230 may be configured to determine a motion vector field based on the first reference data and the second reference data. More descriptions of the determination of the motion vector field may be found elsewhere in the present disclosure (e.g., operation 340 and the descriptions thereof).

The image generation module 240 may be configured to generate a corrected anatomical image matching the PET image by warping/processing the anatomical image based on the motion vector field and generate an attenuation corrected PET image based on the PET image corresponding to the second PET data and the corrected anatomical image. More descriptions of the generation of the corrected anatomical image and the attenuation corrected PET image may be found elsewhere in the present disclosure (e.g., operations 350-360 and the descriptions thereof).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120 may include one or more additional modules, such as a storage module (not shown) for storing data.

Figure 3:
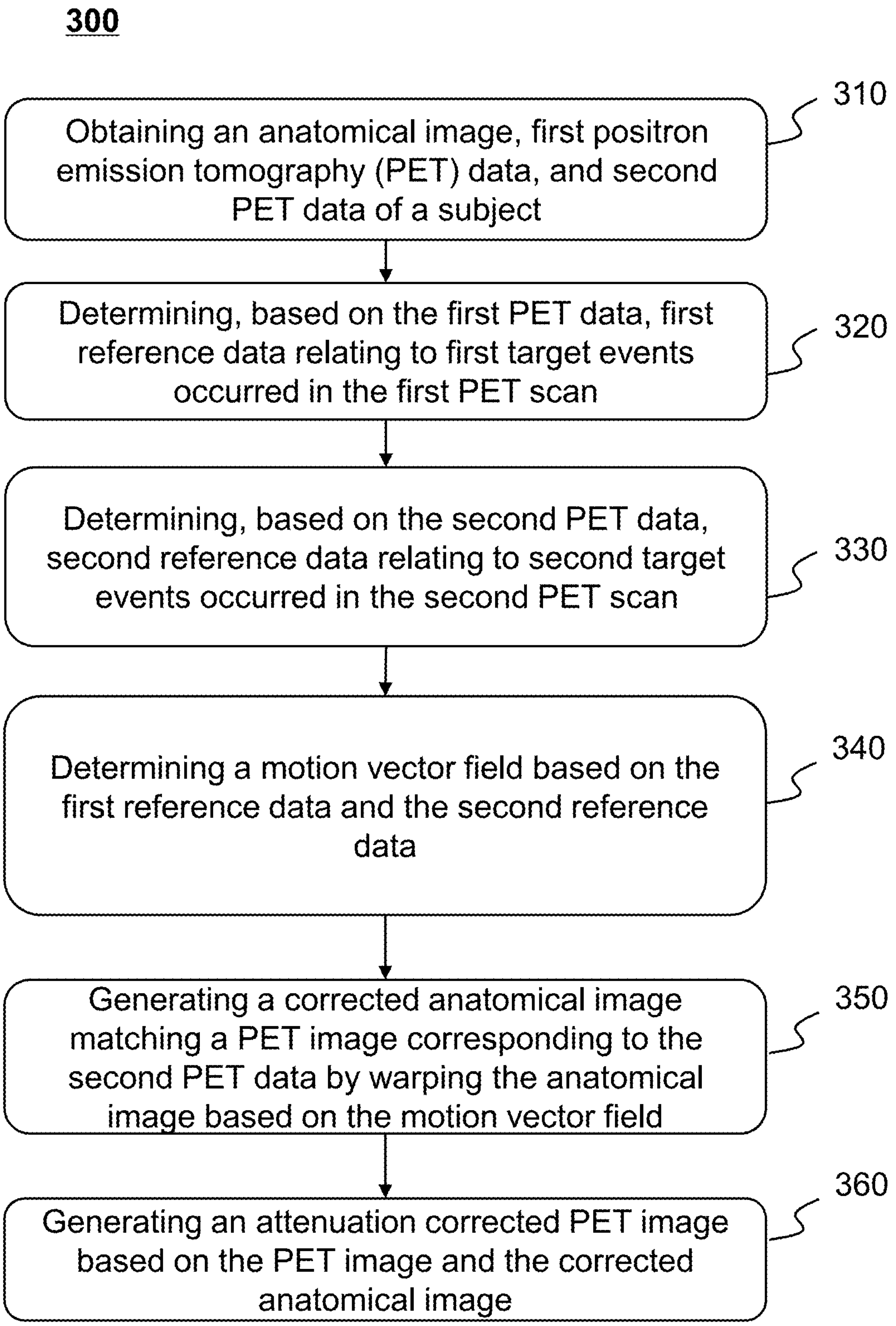
FIG. 3 is a flowchart illustrating an exemplary process for image processing according to some embodiments of the present disclosure.

FIG. 3 is a flowchart illustrating an exemplary process for image processing according to some embodiments of the present disclosure. In some embodiments, process 300 may be executed by the image processing system 100. For example, the process 300 may be implemented as a set of instructions (e.g., an application) stored in a storage device (e.g., the storage device 130), and the processing device 120 (e.g., one or more modules illustrated in FIG. 2) may execute the set of instructions and may accordingly be directed to perform the process 300.

In 310, the processing device 120 (e.g., the obtaining module 210) may obtain an anatomical image, first PET data, and second PET data of a subject.

The first PET data may be collected by a first PET scan performed on the subject at the first time. The first time refers to a time period shorter than a time threshold (e.g., 10 minutes, 1 hour, 1 day), and the first PET scan are performed during the time period. The second PET data may be collected by a second PET scan performed on the subject at a second time. The second time refers to a time period shorter than a time threshold (e.g., 10 minutes, 1 hour, 1 day), and the second PET scan is performed during the time period. It should be noted that the second time may be before or after the first time, that is the second PET scan is performed before or after the first PET scan.

In some embodiments, the anatomical image may be collected by an anatomical scan performed on the subject at the first time. In some embodiments, the anatomical image includes a CT image or an MR image. In some embodiments, the anatomical scan and the first PET scan may be performed by a same scanner (e.g., the scanner 110). The scanner is a PET-CT scanner or a PET-MR scanner. The anatomical scan and the first PET scan are performed simultaneously or successively during the first time. For example, the PET-CT scanner performs the anatomical scan (i.e., a CT scan) and the first PET scan simultaneously or successively during the first time to obtain anatomical data (i.e., CT data) and the first PET data, and the anatomical image may be generated based on the anatomical data. When the anatomical scan and the first PET scan are performed successively, a time interval between the anatomical scan and the first PET scan is not greater than the time threshold. It should be noted that the order in which the anatomical scan and the first PET scan are performed is not limited. The anatomical scan may be performed before or after the first PET scan.

In some embodiments, the anatomical scan and the first PET scan may be performed in a treatment planning stage before a treatment is delivered to the subject. Optionally, a treatment plan may be determined based on the CT image. After the anatomical scan and the first PET scan are performed and the treatment plan is determined based on the CT image, the treatment plan may be delivered to the subject during several treatment sessions, spread over a treatment period of multiple days (e.g., 2 to 5 weeks). During each treatment session, a second PET scan may be performed once to collect a set of second PET data. The second PET data may be any one of multiple sets of second PET data collected during the several treatment sessions. The process 300 may be performed on any one or each of the multiple sets of second PET data.

In some embodiments, the anatomical image may be collected by an anatomical scan performed on the subject at any time other than the first time and the second time. For example, the anatomical scan may be performed in the treatment planning stage, and the first PET scan and the second PET scan may be performed in the treatment period.

In some embodiments, the anatomical scan and the first PET scan may be performed by different scanners. In some embodiments, the scanners may include a PET scanner, a CT scanner, and/or an MR scanner. For example, the PET scanner may perform the first PET scan on the subject first to obtain the first PET data, and then the CT scanner or the MR scanner may perform the anatomical scan on the subject to obtain the anatomical image.

In some embodiments, the processing device 120 may obtain the anatomical image, the first PET data, and second PET data by directing or causing the scanner 110 to perform the anatomical scan, the first PET scan, and the second PET scan on the subject, respectively. In some embodiments, the anatomical image, the first PET data, and second PET data may be previously generated and stored in a storage device (e.g., the storage device 130) disclosed elsewhere in the present disclosure and/or an external storage device. The processing device 120 may obtain the anatomical image, the first PET data, and second PET data from the storage device and/or the external storage device via a network (e.g., the network 150).

In some embodiments, the processing device 120 may determine an initial motion vector field based on the anatomical image and the first PET data, and generate an initial corrected anatomical image matching the first PET image by warping/processing the anatomical image based on the initial motion vector field. Further, the processing device 120 may designate the initial corrected anatomical image as the anatomical image to perform subsequent operations 320-360.

In 320, the processing device 120 (e.g., the reference data determination module 220) may determine, based on the first PET data, first reference data relating to first target events occurred in the first PET scan.

In 330, the processing device 120 (e.g., the reference data determination module 220) may determine, based on the second PET data, second reference data relating to second target events occurred in the second PET scan.

A target event (e.g., the first target event, a second target event) occurs when a first particle and a second particle are detected by crystal units (e.g., opposite crystal units) of the scanner (e.g., the scanner 110) within coincident windows. A detector of the scanner may include a plurality of crystal units, which may detect particles produced in a scan. The coincident windows may relate to an energy and/or a detection time of a particle, and may be used to identify particles produced by a same decay (e.g., a same scattering event, a same background event). In some embodiments, the coincident windows include at least one energy window and at least one time window. An energy window may relate to an energy of a particle, and a time window may relate to a detection time difference between different particles. For example, the coincident windows may include a first energy window, a second energy window, and a time window. The first energy window corresponds to the first particle involved in the first target events and the second target events, and the second energy window corresponds to the second particle involved in the first target events and the second target events. The first energy window may be an energy range of the first particle involved in the first target events and the second target events, the second energy window may be an energy range of the second particle involved in the first target events and the second target events, and the time window may be a range of a detection time difference between the first particle and the second particle involved in the first target events and the second target events.

In some embodiments, the first target events at least include first backscatter events, and the second target events at least include second backscatter events. During a PET scan, an annihilation photon (also referred to as an original annihilation photon) produced by an annihilation event may collide with and be detected by a crystal unit of the scanner, undergo scattering in the crystal unit of the scanner, and be bounced back from the crystal unit and travel through the subject again; the bounced annihilation photon may be detected by another crystal unit. A backscatter event may be detected if the original annihilation photon and the bounced annihilation photon are detected within a certain time window. For backscatter events (e.g., the first backscatter events, the second backscatter events), the first particle is the original annihilation photon, and the second particle is the bounced annihilation photon. The sum of the energy of the original annihilation photon and the energy of the bounced annihilation photon may be close to 511 keV. Based on the simultaneity and different energies of the original annihilation photon and the bounced annihilation photon, a backscatter event may be identified. For example, if the original annihilation photon (i.e., the first particle) and the bounced annihilation photon (i.e., the second particle) are detected by opposite crystal units in the coincident windows, it may be determined that a backscatter event occurs.

In some embodiments, the first target events include first background events, and the second target events include second background events. The first background events and the second background events may be caused by radioactive decay of a crystal material. The crystal units of the scanner may include crystal material that may undergo radioactive decay. For background events (e.g., the first background events, the second background events), the first particle and the second particle may be particles generated by the radioactive decay of the crystal material.

Merely by way of example, the crystal units of the scanner may include a sodium iodide (NaI) crystal unit, a bismuth germanate (BGO) crystal unit, a lutetium silicate (LSO) crystal unit, a yttrium lutetium silicate (LYSO) crystal unit, or the like. The LSO crystal unit and the LYSO crystal unit may include Lu-176, which undergoes radioactive decay. Lu-176 releases particles in the radioactive decay. The radioactive decay of Lu-176 may include a beta decay and a cascade gamma decay. The beta decay may generate a beta electron with an energy in a range of 0 keV~589 keV. The gamma decay may generate three kinds of gamma photons, one having the energy of 307 keV, one having the energy of 202 keV, and the other one having the energy of 88 keV. For background events caused by the radioactive decay of Lu-176, the first particle may be the beta electron or a combination of the beta electron and one or more of the gamma photons (in some occasions, the beta electron and one or more of the gamma photons may be detected by one crystal unit almost at the same time), and the second particle may be one or more of the gamma photons.

If the radioactive decay of Lu-176 occurs in a crystal unit, the beta electron (or the beta electron and one or more of the gamma photons) may be detected in one crystal unit, and one or more of the gamma photons may escape from the crystal unit and be detected by other crystal unit(s). Based on the simultaneity and different energies of the beta electron and the gamma photons, a background event caused by the radioactive decay of Lu-176 may be identified. For example, if a beta electron (i.e., a first particle) and a gamma photon (i.e., the second particle) produced by the radioactive decay of Lu-176 are detected by different crystal units in the coincident windows, it may be determined that a background event occurs.

In some embodiments, the first target events at least include the first backscatter events and the first background events, and the second target events at least include the second backscatter events and the second background events.

In some embodiments, the first reference data relating to first target events includes a sinogram corresponding to the first target events occurred in the first PET scan, and the second reference data relating to second target events includes a sinogram corresponding to the second target events occurred in the second PET scan. In some embodiments, the first reference data may include various information relating to the first target events, and the second reference data may include various information relating to the second target events, such as a first energy of the first particle, a first detection time of the first particle, a second energy of the second particle, a second detection time of the second particle, a position of a crystal unit detecting the first particle, a position of a crystal unit detecting the second particle, or the like, or any combination thereof. In some embodiments, the first reference data may include list mode data, which includes a list of crystal unit information, detection time information, and energy information of each first target event, and the second reference data may include list mode data, which includes a list of crystal unit information, detection time information, and energy information of each second target event. In some embodiments, the first reference data may include data of first target events received by at least one original LOR or combined LOR (e.g., a LOR combined by original LORs), and the second reference data may include data of second target events received by at least one original LOR or combined LOR (e.g., a LOR combined by original LORs).

In some embodiments, the processing device 120 may determine the coincident windows; determine, based on the first PET data and the coincident windows, the first reference data relating to the first target events occurred in the first PET scan; and determine, based on the second PET data and the coincident windows, the second reference data relating to the second target events occurred in the second PET scan. More descriptions of the determination of the first reference data and the second reference data may be found elsewhere in the present disclosure (e.g., FIG. 4 and the descriptions thereof).

In 340, the processing device 120 (e.g., the motion vector field determination module 230) may determine a motion vector field based on the first reference data and the second reference data.

The PET image corresponding to the second PET data refers to an image reconstructed from on the second PET data. The motion vector field may indicate a coordinate transformation/mapping relationship between pixels of the anatomical image and the PET image corresponding to the second PET data. In some embodiments, the motion vector field may include a plurality of motion vectors. A motion vector may be used to describe the motion of two points that correspond to the same spatial point in two images.

In some embodiments, the processing device 120 generates a first attenuation image of the subject based on the first reference data and generates a second attenuation image of the subject based on the second reference data. Further, the processing device 120 may determine the motion vector field based on the first attenuation image and the second attenuation image of the subject. More descriptions of the determination of the motion vector field may be found elsewhere in the present disclosure (e.g., FIG. 5 and the descriptions thereof).

In 350, the processing device 120 (e.g., the image generation module 240) may generate a corrected anatomical image matching the PET image by warping/processing the anatomical image based on the motion vector field.

A corrected anatomical image matching the PET image refers to an anatomical image used to perform attenuation correction for the PET image corresponding to the second PET data. For example, the processing device 120 may generate the corrected anatomical image by adjusting coordinates of the pixels in the anatomical image based on the motion vector field.

According to the embodiments of the present disclosure, the data relating to the first backscatter events and the first PET data are collected at the same time, and the data relating to the second backscatter events and the second PET data are collected at the same time, and the background events are independent of the distribution of the radioactive tracers in the subject, so that there is no risk of image registration failure due to subject movement and high selectivity and specificity of the radioactive tracers. The backscatter events occur during the PET scan (e.g., the first PET scan, the second PET scan), the background events occur in the material of the crystal unit of the scanner, so that no additional radiation dose is added to the subject. The backscatter events and/or the background events are determined based on the PET data (e.g., the first PET data, the second PET data), so that there is no need to add additional acquisition processes and equipment. The background events occur in the LSO and LYSO material of the crystal unit of the scanner, and backscattering events occur in many other crystal materials (e.g., BGO) of the crystal unit of the scanner, so that the image processing methods of process 300 have a wide range of applications.

In 350, the processing device 120 (e.g., the image generation module 240) may generate an attenuation corrected PET image (also referred to as a second corrected PET image) based on the PET image corresponding to the second PET data and the corrected anatomical image.

The processing device 120 may perform attenuation correction on the PET image corresponding to the second PET data based on the corrected anatomical image to generate the attenuation corrected PET image. In some embodiments, the processing device 120 may perform attenuation correction on a PET image corresponding to the first PET data based on the anatomical image to generate an attenuation corrected PET image (also referred to as a first corrected PET image). In some embodiments, the processing device 120 may perform at least one of image segmentation or treatment plan planning based on at least the corrected anatomical image. For example, the processing device 120 may perform the image segmentation on the PET image corresponding to the second PET data based on the corrected anatomical image. As another example, the processing device 120 may perform the treatment plan planning based on the corrected anatomical image or based on the corrected anatomical image and the PET image corresponding to the second PET data.

Figure 4:
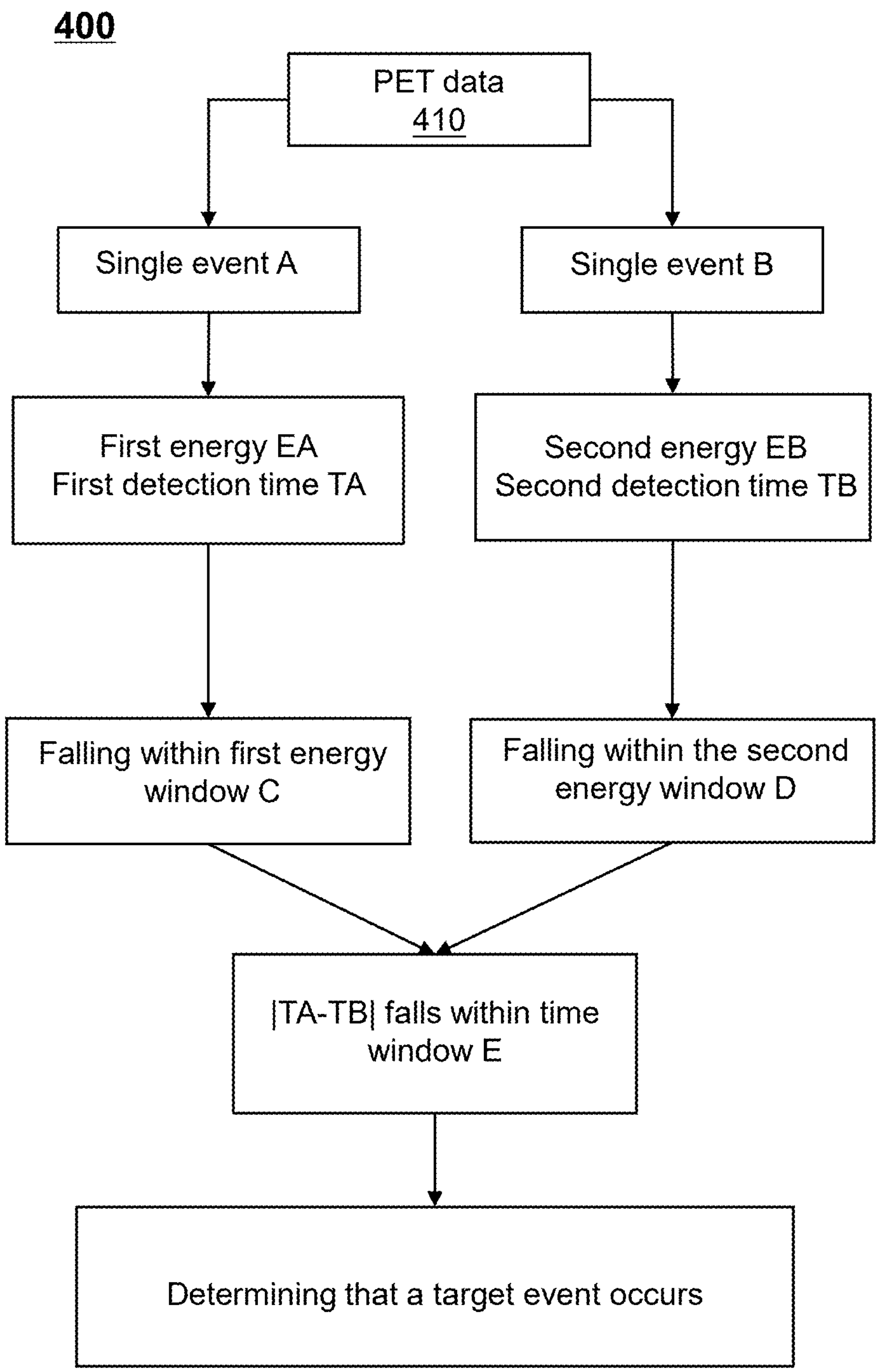
FIG. 4 is a schematic diagram illustrating an exemplary process for determining that a target event occurs according to some embodiments of the present disclosure.

FIG. 4 is a schematic diagram illustrating an exemplary process for determining that a target event occurs according to some embodiments of the present disclosure. In some embodiments, process 400 may be performed to achieve at least part of operations 320-330 as described in connection with FIG. 3.

As shown in FIG. 4, a single event A and a single event B may be determined based on PET data 410 (e.g., the first PET data, the second PET data). The single event A may refer to that a crystal unit of the scanner (e.g., the scanner 110) receives a first particle P1, and the single event B may refer to that another crystal unit of the scanner receives a second particle P2. As used herein, the single event A may occur prior to the single event B. Based on the single event A, a first energy EA and a first detection time TA of the first particle P1 may be determined. Based on the single event B, a second energy EB and a second detection time TB of the second particle P2 may be determined.

Further, the coincident window, including a first energy window C, a second energy window D, and a time window E, may be obtained. As described above, the first energy window C may be an energy range of the first particle involved in the first target events and the second target events, the second energy window D may be an energy range of the second particle involved in the first target events and the second target events, and the time window E may be a range of a detection time difference between the first particle and the second particle involved in the first target events and the second target events.

Then, whether the first particle P1 and the second particle P2 meet a predetermined condition may be determined based on the first energy EA of the first particle P1, the first detection time TA of the first particle P1, the second energy EB of the second particle P2, the second detection time TB of the second particle P2, and the coincident window. In response to determining that the first particle P1 and the second particle P2 meet the predetermined condition, it may be determined that a target event occurs. In response to determining that the first particle P1 and the second particle P2 do not meet the predetermined condition, it may be determined that no target event occurs.

For example, as shown in FIG. 4, if the first energy EA falls within the first energy window C, the second energy EB falls within the second energy window D, and |TA−TB| falls within the time window E, the first particle P1 and the second particle P2 may satisfy the predetermined condition, and the single event A and the single event B may be designated as a target event.

In some embodiments, after PET data of a PET scan (e.g., the first PET data or the second PET data), the processing device 140 may identify target events occurred in the PET scan based on the PET data and the coincident window based on the method described above, and then determine reference data relating to the identified target events (e.g., the first reference data or the second reference data).

In some embodiments, the first energy window C is related to the energy of the first particle P1, and the second energy window D is related to the energy of the second particle P2. In some embodiments, the first energy window C may be [LLD, $E_{1max}+3\sigma$], and the second energy window C may be [LLD, $E_{2max}+3\sigma$]. LLD refers to the lowest energy threshold relating to a deposited energy in a crystal unit, $E_{1max}$ refers to a value larger than or equal to the maximum value of the deposited energy of the first particle P1 in the crystal unit and less than a maximum energy threshold ULD relating to the deposited energy in the crystal unit, $E_{2max}$ refers to a value larger than or equal to the maximum value of the deposited energy of the second particle P2 in the crystal unit and less than the maximum energy threshold ULD relating to the deposited energy in the crystal unit, and $\sigma$ may be a standard deviation of the Gaussian energy distribution. In some embodiments, LLD may be 100 keV, and ULD may be 1023 keV.

For backscatter events, the first particle P1 is the original annihilation photon, and the second particle P2 is the bounced original annihilation photon. Therefore, the maximum value of the deposited energy of the first particle P1 in the crystal unit or the maximum value of the deposited energy of the second particle P2 in the crystal unit is the energy of the original annihilation photon, which is 511 keV. Merely by way of example, for backscatter events, the first energy window C may be [100 keV, 511 keV], [100 keV, 600 keV], [100 keV, 1023 keV], and/or [250 keV, 380 keV], and the second energy window D may be [100 keV, 350 keV], [100 keV, 355 keV], [100 keV, 600 keV], [100 keV, 1023 keV], and/or [100 keV, 250 keV]. Preferably, for backscatter events, the first energy window C may be [250 keV, 380 keV], and the second energy window D may be [100 keV, 250 keV].

For background events, the first particle P1 is the beta electron or the beta electron and one or more of the gamma photons produced by the radioactive decay of Lu-176, and the second particle P2 is one or more of the gamma photons produced by the radioactive decay of Lu-176. The maximum value of the deposited energy of the first particle P1 in the crystal unit is 589 keV or 589 keV+307*n1 keV+202*n2 keV+88*n3 keV, wherein n1, n2, or n3 is zero or a positive integer. The maximum value of the deposited energy of the second particle P2 in the crystal unit is 589 keV+307*n1 keV+202*n2 keV+88*n3 keV, wherein n1, n2, or n3 is zero or a positive integer. Merely by way of example, for background events, the first energy window C may be [100 keV, 589 keV], [100 keV, 896 keV], or [100 keV, 1023 keV], and the second energy window D may be [100 keV, 307 keV], [100 keV, 350 keV], or [100 keV, 614 keV], [250 keV, 350 keV], or [100 keV, 250 keV]. Preferably, for background events, the first energy window C may be [100 keV, 1023 keV], and the second energy window D may be [250 keV, 350 keV] and/or [100 keV, 250 keV].

In some embodiments, the time window E may be [0, $\Delta T_{max}+3\sigma'$], where $\Delta T_{max}$ is a maximum absolute value of the detection time difference between the first particle P1 and the second particle P2. $\sigma'$ is the standard deviation of the Gaussian time distribution. $\sigma'$=FWHM/2.355. FWHM represents the full width at half maximum of a Gaussian function. $\Delta T_{max}$ may be determined based on the propagation speed (i.e., speed of light) of the first particle P1 and the second particle P2, a position of a crystal unit that detects the first particle P1, and a position of a crystal unit that detects the second particle P2. $\Delta T_{max}$ may equal to a distance between the position of the crystal unit that detects the first particle P1 and the position of a crystal unit that detects the second particle P2 divided by the speed of light.

In some embodiments, for backscatter events and the background events, the first energy window C may be [100 keV, 1024 keV], and the second energy window D may be [100 keV, 350 keV].

It should be noted that the descriptions of FIG. 4 are merely for illustration purpose. For those skilled in the art, various changes and modifications may be made under the guidance of the contents of the present disclosure. For example, the coincident window used to determine the target event may be different from the examples provided above. As another example, a background event may be determined based on the radioactive decay of any other crystal materials.

Figure 5:
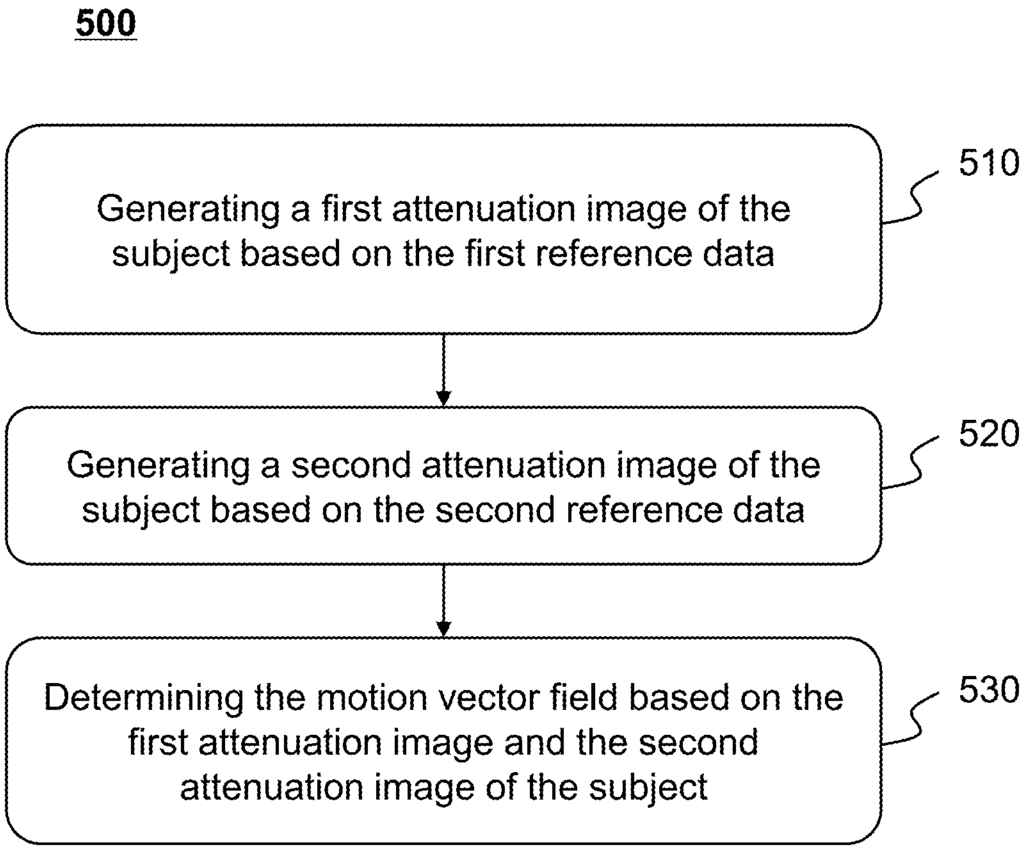
FIG. 5 is a flowchart illustrating an exemplary process for determining a motion vector field according to some embodiments of the present disclosure.

FIG. 5 is a flowchart illustrating an exemplary process for determining a motion vector field according to some embodiments of the present disclosure. In some embodiments, process 500 may be performed to achieve at least part of operation 340 as described in connection with FIG. 3.

In 510, the processing device 120 (e.g., the motion vector field determination module 230) may generate a first attenuation image of the subject based on the first reference data.

In 520, the processing device 120 (e.g., the motion vector field determination module 230) may generate a second attenuation image of the subject based on the second reference data.

For illustration purposes, the generation process of the first attenuation image of the subject based on the first reference data is described herein. The generation process of the second attenuation image may be similarly to the generation process of the first attenuation image, and the descriptions thereof are not repeated here. In some embodiments, the processing device 120 may determine third reference data relating to third target events occurred in a blank scan without the subject, and generate the first attenuation image of the subject based on the third reference data and the first reference data.

In some embodiments, the third target events include third backscatter events. In fact, there is no subject in the blank scan, so the third backscatter events would not occur. Here is the data simulation method to determine the third reference data relating to the third backscatter events. Specifically, the processing device 120 may determine an initial attenuation image and an initial PET image and determine the third reference data relating to the third backscatter events based on the initial attenuation image and the initial PET image. For example, the processing device 120 determines the initial attenuation image by assigning a first average value (e.g., an attenuation value of water) to all pixels of a first image, and determines the initial PET image by assigning a second average value to all pixels of a second image. The first average value and the second average value may be the same or different values. Further, the processing device 120 determines the third reference data relating to the third backscatter events based on the initial attenuation image and the initial PET image using a first processing manner. Merely by way of example, the first processing manner includes a Monte Carlo manner.

In some embodiments, the third target events further include third background events. In such cases, the processing device 120 may obtain blank scan data collected by performing the blank scan without the subject and determine the third reference data relating to the third background events based on the blank scan data. For example, the processing device 120 determine the third reference data relating to the third background events based on the blank scan data and coincident windows for third background events. In some embodiments, the coincident windows for third background events may be the same as the coincident windows for the first background events and the second background events.

In some embodiments, the processing device 120 may generate the first attenuation image of the subject by performing one or more iterations based on the third reference data and the first reference data. Specifically, in each of the one or more iterations, the processing device 120 may determine the initial attenuation image and the initial PET image of the iteration and determine third reference data relating to third target events occurred in a blank scan without the subject based on the initial attenuation image and the initial PET image. Further, the processing device 120 may generate an updated attenuation image by updating the initial attenuation image based on the third reference data and the first reference data and generate an updated PET image by updating the initial PET image based on the updated attenuation image and the first PET data. Further, the processing device 120 may determine whether a termination condition is satisfied. In response to determining that the termination condition is satisfied, the processing device 120 may designate the updated attenuation image as the first attenuation image. In response to determining that the termination condition is not satisfied, the processing device 120 may designate the updated attenuation image and the updated PET image as the initial attenuation image and the initial PET image to be processed in a next iteration.

In some embodiments, the processing device 120 may generate the first attenuation image of the subject based on the third reference data relating to the third backscatter events and the first reference data. In some embodiments, the processing device 120 may generate the first attenuation image of the subject based on the third reference data relating to the third backscatter events and the third reference data relating to the third background events, and the first reference data. More descriptions of the generation of the first attenuation image of the subject may be found elsewhere in the present disclosure (e.g., FIG. 6 and the descriptions thereof).

In 530, the processing device 120 (e.g., the motion vector field determination module 230) may determine the motion vector field based on the first attenuation image and the second attenuation image of the subject.

Specifically, the processing device 120 may determine a motion vector field between the first attenuation image and the second attenuation image by registering the first attenuation image and the second attenuation image, and further designate the motion vector field between the first attenuation image and the second attenuation image as the motion vector field between the anatomical image and the PET image corresponding to the second PET data.

Typically, the image registration requires the use of PET data obtained at the first time and PET data obtained at the other second times. For some PET images acquired with low-doses, the accuracy of the image registration will be significantly reduced. Some highly selective and specific radioactive tracers, such as Zirconium-89 used to label monoclonal antibodies, only can be used to target the location of lesions and do not provide anatomical information, resulting in failure of image registration.

According to the embodiments of the present disclosure, the motion vector field is determined based on the first attenuation image and the second attenuation image, and the first attenuation image and the second attenuation image are less affected by PET image quality, therefore, the image registration has high accuracy.

Figure 6:
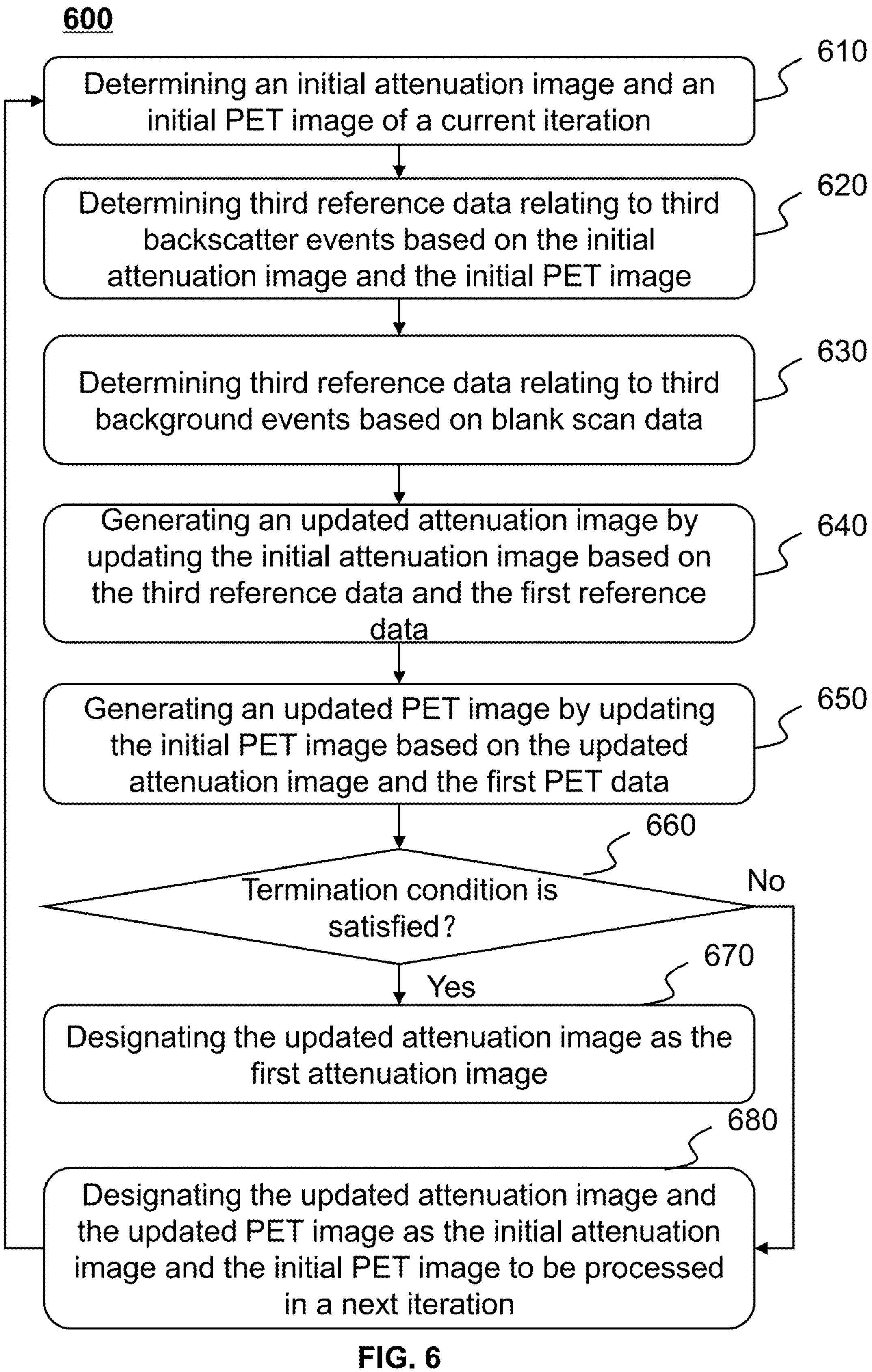
FIG. 6 is a flowchart illustrating an exemplary process for determining an attenuation image according to some embodiments of the present disclosure.

FIG. 6 is a flowchart illustrating an exemplary process for determining the first attenuation image according to some embodiments of the present disclosure. In some embodiments, process 600 may be performed to achieve at least part of operation 510 as described in connection with FIG. 5. The determination process of the first attenuation image includes one or more iterations, and the implementation of a current iteration is described below.

In 610, the processing device 120 (e.g., the motion vector field determination module 230) may determine an initial attenuation image and an initial PET image in the current iteration.

If the current iteration is the first iteration, the processing device 120 may determine the initial attenuation image by assigning a first average value to all pixels of a first image, and determines the initial PET image by assigning a second average value to all pixels of a second image.

If the current iteration is an iteration other than the first iteration, the processing device 120 may designate an updated attenuation image and an updated PET image generated in an iteration immediately preceding the current iteration as the initial attenuation image and the initial PET image, respectively.

More descriptions of the determination of the initial attenuation image and the initial PET image may be found elsewhere in the present disclosure (e.g., operation 520 and the descriptions thereof).

In 620, the processing device 120 (e.g., the motion vector field determination module 230) may determine third reference data relating to third backscatter events based on the initial attenuation image and the initial PET image. More descriptions of the determination of the third reference data relating to the third backscatter events may be found elsewhere in the present disclosure (e.g., operation 520 and the descriptions thereof).

In 630, the processing device 120 (e.g., the motion vector field determination module 230) may determine third reference data relating to third background events based on blank scan data collected by performing blank scan. More descriptions of the determination of the third reference data relating to the third background events may be found elsewhere in the present disclosure (e.g., operation 520 and the descriptions thereof).

In 640, the processing device 120 (e.g., the motion vector field determination module 230) may generate an updated attenuation image by updating the initial attenuation image based on the third reference data and the first reference data.

In some embodiments, the processing device 120 may determine fourth reference data relating to scatter events in the first target events and fifth reference data relating to random events in the first target events. Specifically, the processing device 120 determines the fourth reference data relating to scatter events in the first target events based on the initial attenuation image and the initial PET image using a second processing manner. Merely by way of example, the second processing manner includes a Monte Carlo manner, a single scattering simulation (SSS) manner, an energy-based scatter estimation (EBS) manner, or the like. The processing device 120 determines the fifth reference data relating to random events in the first target events by a delayed window manner or singles rate manner. Further, the processing device 120 may generate the updated attenuation image by updating the initial attenuation image based on the first reference data, the third reference data, the fourth reference data, and the fifth reference data.

In some embodiments, the third reference data used to update the initial attenuation image only includes the third reference data relating to the third backscatter events. Specifically, the processing device 120 may generate the updated attenuation image according to a formula (1) below:

$$\mu_{bs}^{k+1} = \mu_{bs}^{k} + \frac{H^T\left[B_{bs}^k e^{-H\mu_{bs}^k}\left(1 - \frac{y_{bs}}{B_{bs}^k e^{-H\mu_{bs}^k} + s_{bs}^k + r_{bs}}\right)\right]}{H^T\left[\frac{\left(B_{bs}^k e^{-H\mu_{bs}^k}\right)^2}{B_{bs}^k e^{-H\mu_{bs}^k} + s_{bs}^k + r_{bs}} H \cdot 1\right]}, \quad (1)$$

where $$\mu_{bs}^{k+1}$$

refers to the updated attenuation image, $$\mu_{bs}^{k}$$

refers to the initial attenuation image, H refers to a default system matrix, k refers to the current iteration number, $$B_{bs}^{k}$$

refers to the third reference data relating to the third backscatter events, $y_{bs}$ refers to the first reference data, $$s_{bs}^{k}$$

refers to the fourth reference data relating to scatter events in the first backscatter events, and $r_{bs}$ refers to the fifth reference data relating to random events in the first backscatter events.

In some embodiments, the third reference data used to update the initial attenuation image only includes third reference data relating to the third background events. Specifically, the processing device 120 may generate the updated attenuation image according to a formula (2) below:

$$\mu_{Lu}^{k+1} = \mu_{Lu}^{k} + \frac{H^T\left[B_{Lu} e^{-H\mu_{Lu}^k}\left(1 - \frac{y_{Lu}}{B_{Lu} e^{-H\mu_{Lu}^k} + s_{Lu}^k + r_{Lu}}\right)\right]}{H^T\left[\frac{\left(B_{Lu} e^{-H\mu_{Lu}^k}\right)^2}{B_{Lu} e^{-H\mu_{Lu}^k} + s_{Lu}^k + r_{Lu}} H \cdot 1\right]}, \quad (2)$$

where $$\mu_{Lu}^{k+1}$$

refers to the updated attenuation image, $$\mu_{Lu}^{k}$$

refers to the initial attenuation image, H refers to a default system matrix, k refers to current iteration number, $B_{Lu}$ refers to the third reference data relating to the third background events, $y_{Lu}$ refers to the reference data, $$s_{Lu}^{k}$$

refers to the fourth reference data relating to scatter events in the background events (e.g., the first background events, the second background events), and $r_{Lu}$ refers to the fifth reference data relating to random events in the background events (e.g., the first background events, the second background events).

In some embodiments, the third reference data used to update the initial attenuation image includes the third reference data relating to the third backscatter events and the third background events. Specifically, the processing device 120 may generate the updated attenuation image according to a formula (3) below:

$$\mu_{all}^{k+1}=\mu_{all}^{k}+\frac{H^T\left[e^{-H\mu_{all}^k}\left(1-\frac{y_{all}}{B_{all}^k e^{-H\mu_{all}^k}+s_{all}^k+r_{all}}\right)\right]}{H^T\left[\frac{\left(B_{all}^k e^{-H\mu_{all}^k}\right)^2}{B_{all}^k e^{-H\mu_{all}^k}+s_{all}^k+r_{all}}H\cdot 1\right]}, \quad (3)$$

where $$\mu_{all}^{k+1}$$

refers to the updated attenuation image, $$\mu_{all}^{k}$$

refers to the initial attenuation image, H refers to a default system matrix, k refers to current iteration number, $$B_{all}^k=B_{bs}^k+B_{Lu},\ y_{all}=y_{bs}+y_{Lu},\ s_{all}^k=s_{bs}^k+s_{Lu}^k,\ \text{and}\ r_{all}=r_{bs}+r_{Lu}.$$

According to the embodiments of the present disclosure, the updated attenuation image is generated by making full use of different types of events, which can improve the signal-to-noise ratio of the generated updated attenuation image and thus the accuracy of the subsequently generated attenuation image, thereby improving the accuracy of the motion vector field determined based on the first attenuation image and the second attenuation image, and accordingly improving the accuracy of the image registration.

In 650, the processing device 120 (e.g., the motion vector field determination module 230) may generate an updated PET image by updating the initial PET image based on the updated attenuation image and the first PET data.

In some embodiments, the processing device 120 may determine sixth reference data relating to scatter events in the first PET data and seventh reference data relating to random events in the first PET data. Specifically, the processing device 120 determines the sixth reference data based on the initial attenuation image and the initial PET image using a third processing manner. Merely by way of example, the third processing manner includes a Monte Carlo manner, a single scattering simulation (SSS) manner, an energy-based scatter estimation (EBS) manner, or the like. Further, the processing device 120 may generate the updated PET image by updating the initial PET image based on the updated attenuation image, the first PET data, the sixth reference data, and the seventh reference data.

Specifically, the processing device 120 may generate the updated PET image according to a formula (4) below:

$$\lambda^{k+1}=\frac{\lambda^k}{(A^kH)^T\cdot 1}H^T\frac{y_{emission}}{H\lambda^k+\frac{ss^k+rr}{A^k\cdot 1}},\ A^k=\mathrm{diag}\left(e^{-H\mu_*^k}\right), \quad (4)$$

where $\lambda^{k+1}$ refers to the updated PET image, $\lambda^k$ refers to the initial PET image, H refers to a default system matrix, k refers to the current iteration number, $y_{emission}$ refers to the first PET data, ss refers to the sixth reference data, rr refers to the seventh reference data, and $\mu_*^k$ is $\mu_{bs}^k$, $\mu_{Lu}^k$, or $\mu_{all}^k$.

According to the embodiments of the present disclosure, the updated PET image is generated by making full use of different types of events, which can improve the signal-to-noise ratio of the updated PET image, the accuracy of the determined third reference data in a next iteration, and thus the accuracy of the subsequently generated updated attenuation image in the next iteration, thereby improving the accuracy of the final determined motion vector field, and accordingly improving the accuracy of the image registration.

In 660, the processing device 120 (e.g., the motion vector field determination module 230) may determine whether a termination condition is satisfied.

In some embodiments, the termination condition includes a pre-specified number of iterations have been performed, a difference in updated PET images in two adjacent iterations being less than a preset threshold, a difference in attenuation effect sinograms in two adjacent iterations being less than a certain threshold, etc. As used herein, the attenuation effect sinograms refer to forward projections of updated attenuation images in the two adjacent iterations.

In 670, in response to determining that the termination condition is satisfied, the processing device 120 (e.g., the motion vector field determination module 230) may designate the updated attenuation image as the first attenuation image.

In 680, in response to determining that the termination condition is not satisfied, the processing device 120 (e.g., the motion vector field determination module 230) may designate the updated attenuation image and the updated PET image as the initial attenuation image and the initial PET image to be processed in a next iteration, and then perform operations 610-660 again.

Figure 7:
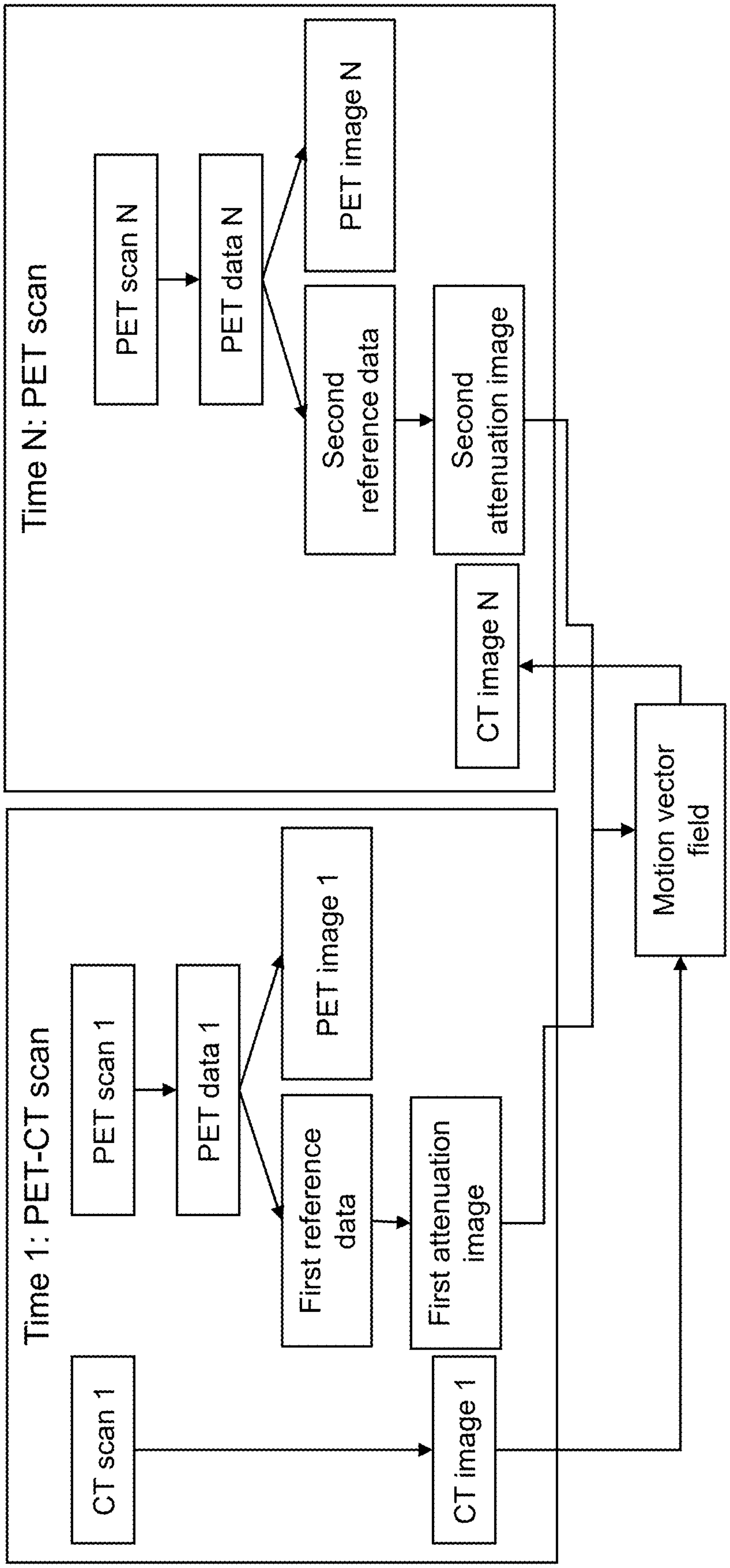
FIG. 7 is a schematic diagram illustrating an exemplary process for image processing according to some embodiments of the present disclosure.
Figure 8:
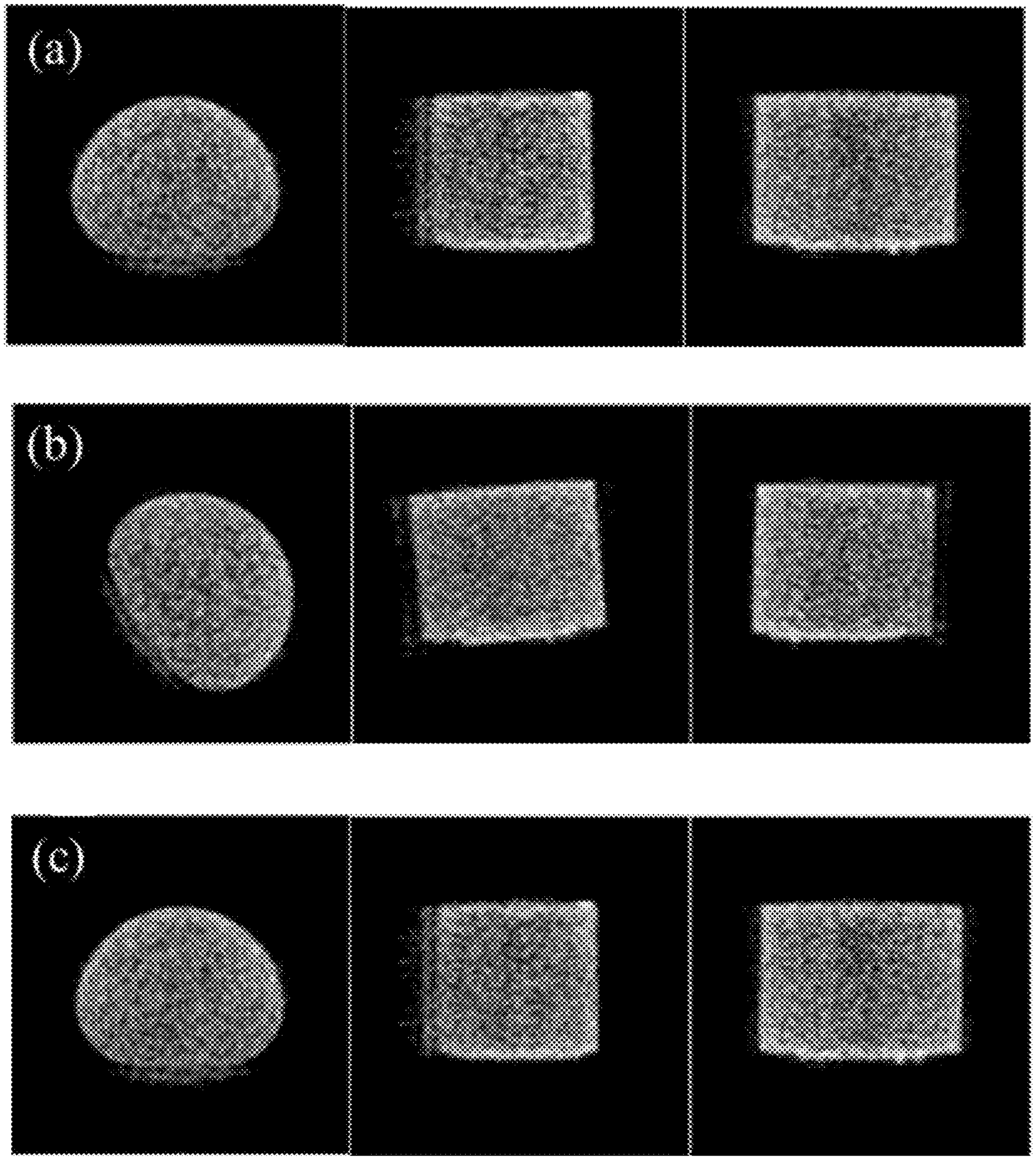
FIG. 8 is a schematic diagram illustrating an exemplary first attenuation image, an exemplary second attenuation image, and an exemplary corrected anatomical image system according to some embodiments of the present disclosure.
Figure 9:
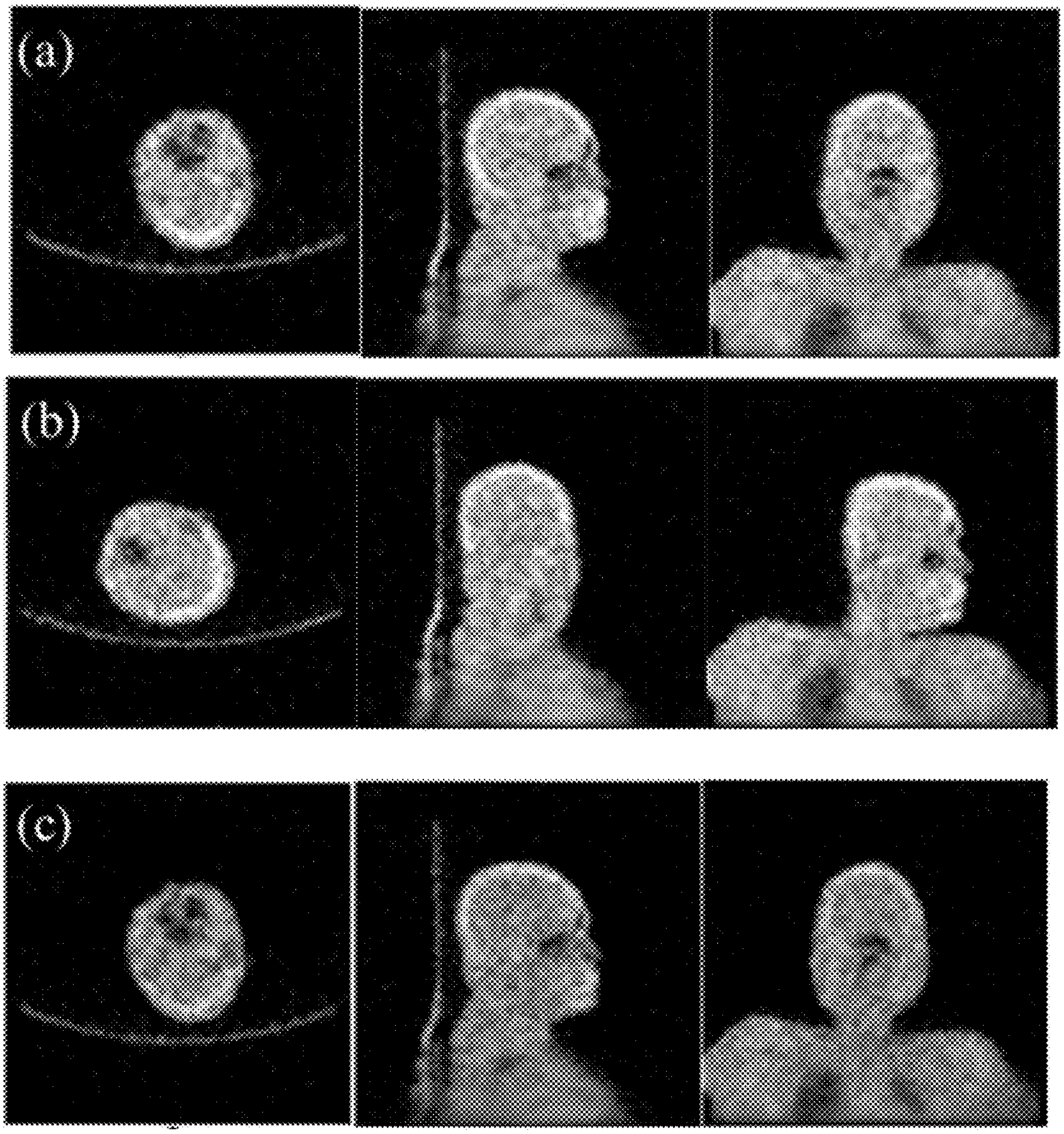
FIG. 9 is a schematic diagram illustrating an exemplary first attenuation image, an exemplary second attenuation image, and an exemplary corrected anatomical image according to some embodiments of the present disclosure.

FIG. 7 is a schematic diagram illustrating an exemplary process for image processing according to some embodiments of the present disclosure. As shown in FIG. 7, a PET-CT scan (including a CT scan 1 and a PET scan 1) may be performed at time 1 to collect a CT image 1 and PET data 1 of a subject. Based on the PET data 1, a PET image 1 and first reference data relating to first target events (e.g., the first backscatter events, the first background events) occurred in the PET scan 1 may be determined. Afterward, a PET scan N is performed at time N to collect PET data N of the subject. Based on the PET data N, a PET image N and second reference data relating to second target events (e.g., the second backscatter events, the second background events) occurred in the PET scan N may be determined. A first attenuation image of the subject may be generated based on the first reference data, and a second attenuation image of the subject may be generated based on the second reference data. As shown in FIG. 8 and FIG. 9, images (a) are exemplary first attenuation images, images (b) are exemplary second attenuation images.

Based on the first attenuation image and the second attenuation image of the subject, a motion vector field may be determined. A CT image N matching the PET image N may be generated by warping/processing the CT image 1 based on the motion vector field. As shown in FIG. 8 and FIG. 9, images (c) are exemplary warped attenuation images (e.g., the CT image N) using the determined motion field. Further, attenuation correction may be performed on the PET image 1 based on the CT image to generate an attenuation corrected PET image 1, and attenuation correction may be performed on the PET image N based on the CT image N to generate an attenuation corrected PET image N.

The operations of the illustrated processes 300, 400, 500, and 600 presented above are intended to be illustrative. In some embodiments, a process may be accomplished with one or more additional operations not described, and/or without one or more of the operations discussed. Additionally, the order in which the operations of a process described above is not intended to be limiting.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" may mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.), or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python, or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer, and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for image processing, implemented on a computing device having at least one processor and at least one storage device, comprising:

obtaining first positron emission tomography (PET) data and second PET data of a subject;

determining, based on the first PET data, first reference data relating to first target events occurred in the first PET scan, the first target events at least including first backscatter events;

determining, based on the second PET data, second reference data relating to second target events occurred in the second PET scan, the second target events at least including second backscatter events; and determining a motion vector field based on the first reference data and the second reference data, wherein each backscatter event of the first backscatter events and the second backscatter events occurs when an original annihilation photon and a bounced annihilation photon are respectively detected by a first crystal unit and a second crystal unit of a PET scanner within a time window, the original annihilation photon is detected by the first crystal unit and undergoes scattering in the first crystal unit, resulting in the bounced annihilation photon that escapes the first crystal unit, travels back through the subject, and is detected by the second crystal unit.

2. The method of claim 1, wherein the first target events further include first background events, the second target events further include second background events, the first background events and the second background events are caused by radioactive decay of a crystal material.

3. The method of claim 1, wherein the first reference data and the second reference data are determined by:

determining coincident windows, the coincident windows including a first energy window, a second energy window, and a time window;

determining, based on the first PET data and the coincident windows, the first reference data relating to the first target events occurred in the first PET scan; and determining, based on the second PET data and the coincident windows, the second reference data relating to the second target events occurred in the second PET scan.

4. The method of claim 1, wherein the determining a motion vector field based on the first reference data and the second reference data includes:

generating a first attenuation image of the subject based on the first reference data;

generating a second attenuation image of the subject based on the second reference data; and determining the motion vector field based on the first attenuation image and the second attenuation image of the subject.

5. The method of claim 4, wherein the generating a first attenuation image of the subject based on the first reference data includes one or more iterations, each of the iterations comprises:

determining an initial attenuation image and an initial PET image of the iteration;

determining third reference data relating to third target events occurred in a blank scan without the subject based on the initial attenuation image and the initial PET image;

generating an updated attenuation image by updating the initial attenuation image based on the third reference data and the first reference data;

generating an updated PET image by updating the initial PET image based on the updated attenuation image and the first PET data; and determining the first attenuation image of the subject based on the updated PET image.

6. The method of claim 5, wherein the third target events include third backscatter events and third background events, and the determining third reference data includes:

determining the third reference data relating to the third backscatter events based on the initial attenuation image and the initial PET image;

obtaining blank scan data collected by performing the blank scan; and determining the third reference data relating to the third background events based on the blank scan data.

7. The method of claim 5, wherein each iteration further comprises:

determining fourth reference data relating to scatter events in the first target events and fifth reference data relating to random events in the first target events, wherein the updated attenuation image is determined further based on the fourth reference data and the fifth reference data.

8. The method of claim 5, wherein the fourth reference data relating to scatter events is determined based on an initial attenuation image and an initial PET image using a processing manner selected from a Monte Carlo manner, a single scattering simulation manner, or an energy-based scatter estimation (EBS) manner;

the fifth reference data relating to random events is determined by a delayed window manner or a single rate manner.

9. The method of claim 1, further comprising:

obtaining an anatomical image;

generating a corrected anatomical image matching a PET image corresponding to the second PET data by processing the anatomical image based on the motion vector field; and generating an attenuation corrected PET image based on the PET image and the corrected anatomical image.

10. The method of claim 9, wherein the anatomical image includes a computed tomography (CT) image or a magnetic resonance (MR) image.

11. The method of claim 9, wherein the first PET data is collected by a first PET scan performed on the subject at a first time, and the second PET data is collected by a second PET scan performed on the subject at a second time.

12. The method of claim 11, wherein the anatomical image is collected by an anatomical scan performed on the subject at the first time.

13. The method of claim 11, wherein the anatomical image is collected by an anatomical scan performed on the subject at any time other than the first time and the second time.

14. The method of claim 11, wherein the second time is before or after the first time, and the second PET scan is performed before or after the first PET scan.

15. The method of claim 1, further comprising:
obtaining an anatomical image;
generating a corrected anatomical image matching a PET image corresponding to the second PET data by processing the anatomical image based on the motion vector field; and
performing at least one of image segmentation or treatment plan planning based on at least the corrected anatomical image.

16. A system, comprising:
at least one storage device including a set of instructions; and
at least one processor in communication with the at least one storage device, wherein when executing the set of instructions, the at least one processor causes the system to perform operations including:
obtaining first positron emission tomography (PET) data and second PET data of a subject;
determining, based on the first PET data, first reference data relating to first target events occurred in the first PET scan, the first target events at least including first backscatter events;
determining, based on the second PET data, second reference data relating to second target events occurred in the second PET scan, the second target events at least including second backscatter events; and
determining a motion vector field based on the first reference data and the second reference data by:
generating a first attenuation image of the subject based on the first reference data;
generating a second attenuation image of the subject based on the second reference data; and
determining the motion vector field based on the first attenuation image and the second attenuation image of the subject.

17. The system of claim 16, wherein the first target events further include first background events, the second target events further include second background events, the first background events and the second background events are caused by radioactive decay of a crystal material.

18. The system of claim 16, wherein the first reference data and the second reference data are determined by:
determining coincident windows, the coincident windows including a first energy window, a second energy window, and a time window;
determining, based on the first PET data and the coincident windows, the first reference data relating to the first target events occurred in the first PET scan; and
determining, based on the second PET data and the coincident windows, the second reference data relating to the second target events occurred in the second PET scan.

19. The system of claim 16, wherein each backscatter event of the first backscatter events and the second backscatter events occurs when an original annihilation photon and a bounced annihilation photon are respectively detected by a first crystal unit and a second crystal unit of a PET scanner within a time window,
the original annihilation photon is detected by the first crystal unit and undergoes scattering in the first crystal unit, resulting in the bounced annihilation photon that escapes the first crystal unit, travels back through the subject, and is detected by the second crystal unit.

20. A non-transitory computer readable medium, comprising executable instructions that, when executed by at least one processor, direct the at least one processor to perform a method, the method comprising:
obtaining first positron emission tomography (PET) data and second PET data of a subject;
determining, based on the first PET data, first reference data relating to first target events occurred in the first PET scan, the first target events at least including first backscatter events;
determining, based on the second PET data, second reference data relating to second target events occurred in the second PET scan, the second target events at least including second backscatter events; and
determining a motion vector field based on the first reference data and the second reference data, wherein each backscatter event of the first backscatter events and the second backscatter events occurs when an original annihilation photon and a bounced annihilation photon are respectively detected by a first crystal unit and a second crystal unit of a PET scanner within a time window,
the original annihilation photon is detected by the first crystal unit and undergoes scattering in the first crystal unit, resulting in the bounced annihilation photon that escapes the first crystal unit, travels back through the subject, and is detected by the second crystal unit.

* * * * *